United States Patent
Haberland et al.

(10) Patent No.: US 6,425,861 B1
(45) Date of Patent: Jul. 30, 2002

(54) SYSTEM AND METHOD FOR MONITORING AND CONTROLLING A PLURALITY OF POLYSOMNOGRAPHIC DEVICES

(75) Inventors: Ben Haberland, Palm City, FL (US); Yves Berquin, Brussels; Didier Michel, Linkebeek, both of (BE)

(73) Assignee: Respironics, Inc., Pittsburgh, PA (US)

( * ) Notice: Subject to any disclaimer, the term of this patent is extended or adjusted under 35 U.S.C. 154(b) by 0 days.

(21) Appl. No.: 09/454,374

(22) Filed: Dec. 3, 1999

Related U.S. Application Data

(60) Provisional application No. 60/111,149, filed on Dec. 4, 1998.

(51) Int. Cl.[7] .................................................. A61B 5/00
(52) U.S. Cl. ..................................................... 600/300
(58) Field of Search .................................. 600/300, 301, 600/484, 324, 587, 515, 528, 529, 549; 374/142; 128/204.26, 204.23, 204.21, 904

(56) References Cited

U.S. PATENT DOCUMENTS

| | | | | |
|---|---|---|---|---|
| 4,129,125 A | * | 12/1978 | Lester et al. ................. | 600/484 |
| 5,275,159 A | * | 1/1994 | Griebel ......................... | 600/324 |
| 5,544,649 A | * | 8/1996 | David et al. ................. | 600/301 |
| 5,823,187 A | * | 10/1998 | Estes et al. ............. | 128/204.23 |

OTHER PUBLICATIONS

Respironics' "ALICE 3® Infant and Adult Computerized Polysomnographic System User's Guide," 577–8149–00 Rev. B.

* cited by examiner

*Primary Examiner*—Eric F. Winakur
*Assistant Examiner*—Brian Szmal
(74) *Attorney, Agent, or Firm*—Troutman Sanders LLP; Gerald R. Boss

(57) ABSTRACT

A polysomnographic system is provided for use in conjunction with a communications network to simultaneously perform sleep studies on a plurality of patients. The polysomnographic system includes a first remote polysomnographic unit for collecting physiological data from a first patient and a second remote polysomnographic unit for collecting physiological data from a second patient. The first and second remote polysomnographic units communicate with a host unit which allows for remote observation and manipulation of sensors and therapeutic devices unit via a communication network. An affiliated pressure support device is controlled if obstructive sleep apnea is present.

10 Claims, 5 Drawing Sheets

SYSTEM AND METHOD FOR MONITORING AND CONTROLLING A PLURALITY OF POLYSOMNOGRAPHIC DEVICES

This application claims priority from U.S. Provisional Application No. 60/111,149 entitled "Method and Apparatus for Sleep Monitoring and Therapy," filed on Dec. 4, 1998.

BACKGROUND OF THE INVENTION

1. Field of Invention

This invention generally relates to a method and apparatus for monitoring and treating sleep disorders, and, more particularly, to a computerized polysomnographic system for simultaneously monitoring a plurality of patients undergoing respective sleep studies and for controlling a pressure support device for each individual patient, either treating a patient or for determining a prescription for treatment of a patient having a breathing disorder, such as sleep apnea.

2. Description of Related Art

There are three recognized types of sleep apnea. Central sleep apnea is characterized by the suspension of all respiratory movement and is generally believed to be neurological in origin. Obstructive sleep apnea is characterized by the collapse of the upper airways during sleep. The third type of sleep apnea is a combination of central and obstructive sleep apnea and is known as mixed apnea. Individuals having sleep apnea often are only able to sleep for short periods of time before interruption by apneic episodes and, therefore, are only able to obtain fragmented and intermittent sleep. As a result, sleep apnea can cause a host of secondary symptoms, such as general fatigue and daytime sleepiness, high blood pressure, cognitive dysfunction, cardiac arrhythmia, and even congestive heart failure. It is estimated that between 1% and 5% of the general population are afflicted with some level of sleep apnea.

Treatments for sleep apnea have included a number of pharmacological agents and several surgical procedures such as tracheostomy or the removal of excess muscle and tissue from the tongue or airway walls. However, pharmacological treatments for sleep apnea have been generally ineffective and may have adverse side effects. Furthermore, the surgical procedures involve major surgery which may cause extreme discomfort and may involve significant risk of postoperative complications.

Another, less invasive and more effective method for treating obstructive sleep apnea involves the use of continuous positive airway pressure ("CPAP") to prevent obstruction of the patient's airway during sleep. In CPAP, air is generally provided to the patients airway via a nasal mask at a selected pressure or pressures. If too much air is provided, the patient will experience discomfort and is likely to discontinue the treatment. If too little air is provided, the occlusion will not be prevented from occurring and the patient will continue to experience apneic episodes.

Accordingly, it is usually necessary to perform a calibration in order to determine the therapeutic delivery of gas pressure and gas flow provided to each patient who is to receive nasal-CPAP treatment. Calibration is generally performed by a sleep technician as a part of a sleep study of the patient. During the sleep study, the technician monitors a number of the patient's physiological parameters via a polysomnographic device and manipulates the operating parameters of nasal-CPAP device in response to the data sensed by a in order to optimize the parameters for the specific patient if obstructive sleep apnea appears to occur. Typically, the technician observes the individual being treated with the nasal-CPAP treatment and manipulates the airflow and pressure from the nasal-CPAP device to progressively increase it until no further breathing abnormalities or other evidence of upper airway occlusions or resistance are observed. Sleep studies also may be performed to investigate and diagnose the sleep behavior of individuals who are suffering from other sleeping disorders.

During a sleep study, a polysomnographic device is used to monitor certain of the individual's physiological parameters to allow a determination of whether the individual suffers from any physiological impairment that hinders the individual's sleep pattern. Typically, the monitored parameters include such things as electrical encephalographic activity (EEG); eye movements, muscle activity, heart rhythm (ECG), respiratory effort, nasal and/or oral airflow, blood oxygen saturation ($SpO_2$), body position, limb movements, exhalation $CO_2$, esophageal pH; and breathing sounds (for snoring). These parameters are typically each monitored by sensors that produce analog signals which are then transmitted to a control/display unit for presentation to a sleep technician.

An example of a polysomnographic device is the Alice® 3 polysomnographic system developed by Respironics, Inc. of Pittsburgh, Pa. The Alice® 3 system incorporates a number of sensors attached to a sensor input box. The signals are transferred to an amplifier which amplifies, conditions and digitizes the signals. From the amplifier, the digital signals are sent to a standalone computer wherein software displays the signals in a manner designated by a sleep technician. From the signals, sleep disorders are diagnosed. After the airway becomes obstructed, the obstruction is usually not relieved until the individual arouses from sleep. A typical polysomnographic system, such as the Alice® 3 system, can only be used to monitor the parameters of a single patient.

During the therapeutic stage of the sleep study, while the polysomnographic apparatus monitors and displays the sleep information from the individual if obstructive sleep apnea appears present, a sleep technician is required to attend each individual patient in order to manipulate an independent nasal-CPAP device in conjunction with monitoring the polysomnographic apparatus and observe the impact of the manipulation of various pressures induced by the nasal-CPAP device. This situation, while suitable for its intended purpose, results in the need for a one-to-one ratio of sleep technicians and sleep patients. However, because sleep studies are often performed in hospitals and sleep labs, which are typically conducting multiple simultaneous studies, it would be desirable to decrease the number of sleep technicians required in order to reduce the overall operating costs of the sleep study facility. Thus, there is a need for a system allowing a single sleep technician to perform simultaneous sleep studies on multiple patients.

Accordingly, it is an object of the present invention to provide a polysomnographic apparatus that enables a single technician to conduct multiple sleep studies simultaneously.

Furthermore, it is an object of the present invention to provide a polysomnographic apparatus that enables a single technician to monitor sleep related data from several patients simultaneously while also being able to control the operation of a positive pressure support device for each individual patient for diagnosing obstructive sleep apnea or determining a therapeutic prescription for treating an obstructive sleep apneic occurrence.

It is yet another object of the present invention to provide a polysomnographic apparatus that may be used by a sleep technician to monitor and adjust the therapy of one or more patients who are sited at remote locations.

SUMMARY OF THE INVENTION

The above objectives are accomplished according to the present invention by providing a polysomnographic system for use in conjunction with a communications network. The polysomnographic system includes a first remote unit for collecting physiological data from a first patient. The first remote unit includes a first sensor for detecting a physiological parameter of the first patient and generating a first parameter indicating signal in response thereto, which is communicated to the communications network via a first communications interface. The polysomnographic system also includes a second remote unit for collecting physiological data from a second patient. The second remote unit includes a second sensor for detecting a physiological parameter of the second patient and generating a second parameter indicating signal in response thereto, which is communicated to the communications network via a second communications interface. The polysomnographic device includes a host unit for receiving the first and second parameter indicating signals via the communication network and for displaying information indicative of the first and second parameters to an operator.

BRIEF DESCRIPTION OF THE DRAWINGS

The construction and design to carry out the invention will hereinafter be described together with other features thereof. The invention will be more readily understood from a reading of the following specification and by reference to the accompanying drawings forming a part thereof, wherein an example of the invention is shown and wherein.

DETAILED DESCRIPTION OF PREFERRED EMBODIMENTS

Figure 1:
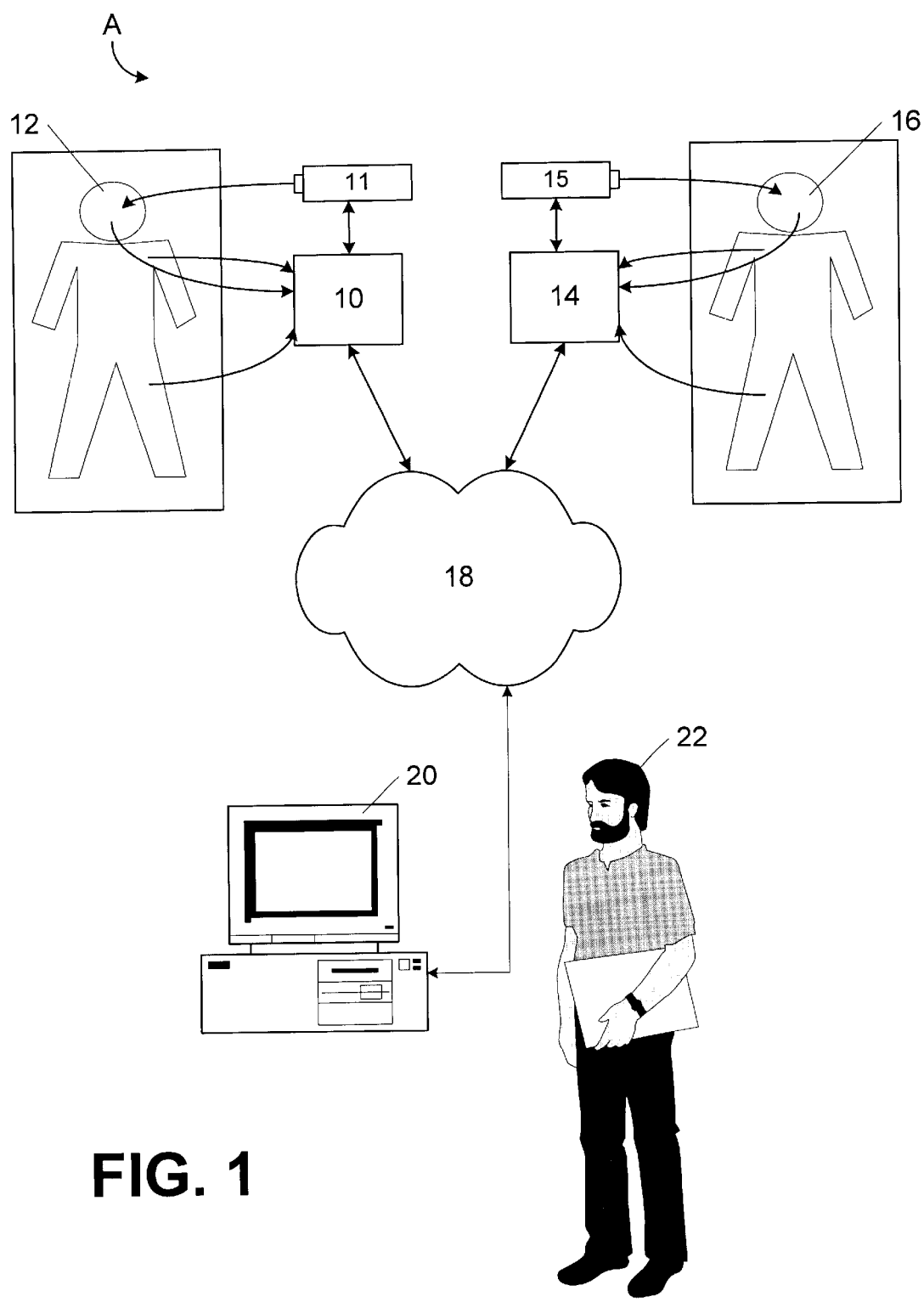
FIG. 1 is a schematic view of a system for monitoring and controlling a plurality of polysomnographic devices in accordance with a preferred embodiment of the present invention.

Referring now to the drawings, the invention will now be described in detail. As shown in FIG. 1, in a preferred embodiment, polysomnographic system A includes a first remote polysomnographic unit 10 for collecting physiological data from a first patient 12 and a second remote polysomnographic unit 14 for collecting physiological data from a second patient 16. First remote polysomnographic unit 10 and second remote polysomnographic unit 14 are each operative to relay parameter indicative signals representing patient physiological parameters via bi-directional communication network 18 to a host unit 20. Host unit 20 is operative to process the physiological data indicative signals and to display data indicative of the patients' physiological status to a sleep technician 22. Host unit 20 is also operative to generate control signals for controlling the operation of first pressure support unit 11 and second pressure support unit 15 which are disposed to provide therapeutic gas flow to first patient 12 and second patient 16 respectively. One type of pressure support unit is the Tranquility® manufactured by Respironics, Inc. of Pittsburgh, Pa. Of course any pressure support device capable of being remotely controlled may be used such as a continuous positive airway pressure support device or a bi-level pressure support device.

Figure 2:
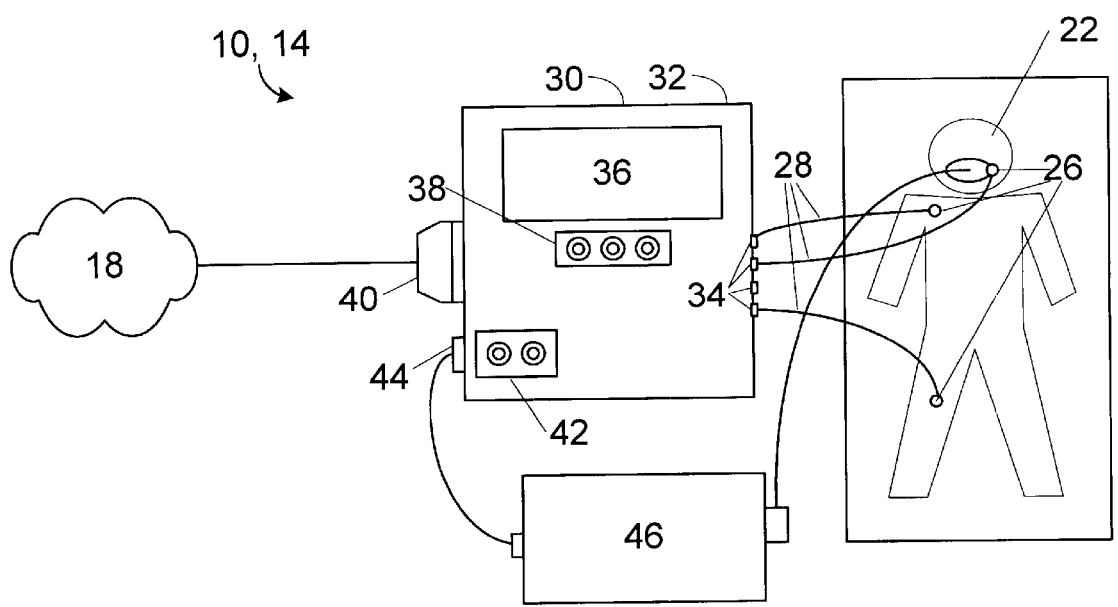
FIG. 2 is a schematic view of the a remote polysomnographic unit in accordance with the embodiment of FIG. 1.

As shown in FIG. 2, each remote polysomnographic unit 10 and 14 includes a plurality of sensors 26 that are operatively connected via sensor cables 28 to a polysomnographic monitor 30. Polysomnographic monitor 30 includes a housing 32 carrying a plurality of sensor cable connections 34 for receiving sensor cables 28, a local display 36 for displaying data to a local operator, a plurality of sensor controls 38 for adjusting the operation and signal gain of sensors 26, and a communications interface 40 for allowing bi-directional communication with communication network 18. In a preferred embodiment, polysomnographic monitor 30 also includes therapeutic controls 42 and auxiliary port 44 for allowing an operator to, either locally or remotely, control the operation of an auxiliary therapeutic device 46 which may provide positive airway pressure to the patient.

Sensors 26 are operative to measure certain physiological parameters of the patient 22 and generate analog signals indicative of the measured parameters. Preferably, the physiological parameters measured by sensors 26 are selected from a group of parameters known to be associated with physiological impairments which may hinder the sleep patterns of individuals. Typically, the monitored parameters include: global neural electrical encephalographic activity (EEG) from electrodes placed on the patient's scalp; eye movements (electro-oculogram or EOG) from electrodes placed near the patient's eyes; submental electromyographic activity (EMG) from electrodes placed over selected muscles; heart rhythm via electrocardiogram (ECG); respiratory effort as measured by chest-wall or abdominal movement sensors; nasal and/or oral airflow via thermistor or pneumotachograph; oxygen saturation ($SpO_2$) via pulse oximetry; body position via mercury switches or direct observation; limb movements via EMG; end-tidal CO2 from the patients exhaled air; transcutaneous CO2; esophageal pH; and breathing sounds (for snoring).

Analog signals generated by sensors 26 are communicated to polysomnographic monitor 30 through sensor cables 28, which are connectable thereto via sensor cable connections 34. Polysomnographic monitor 30 contains circuitry and software necessary to amplify the parameter indicative signals and to control the gain of the signals in response to local or remote operator manipulation of sensor controls 38. Polysomnographic monitor 30 also contains an analog to digital converter and other circuitry and software necessary for digitizing and manipulating the parameter indicative signals into a format suitable for communication via communication network 18. Polysomnographic monitor 30 further contains circuitry and software necessary to display parameter indicative signals to a local operator via local display 36. In a preferred embodiment, a local operator may use local display 36 to view readings from sensors 26 during the diagnostic therapeutic stages of a sleep study. The local operator then may control the sensors 26 via auxiliary controls 38 which include a touch screen and/or a keyboard and mouse.

Polysomnographic monitor 30 includes communication interface 40 for allowing bi-directional communication of data with communication network 18 and therethrough to host unit 20. Bi-directional communication network 18 may consist of any commonly used type of bi-directional communications such as a telephone network, the Internet, an intranet, a local area network, a wide area network, direct connection via dedicated cables, or a wireless network. In the preferred embodiment, communication network 18 is an Ethernet-type local area network and communication interface 40 is a standard Ethernet network interface card.

In a preferred embodiment, the circuitry and software of polysomnographic monitor 30 are responsive to control signals received from host unit 20 for allowing remote control of the operation of sensors 26 and the signal gain of parameter indicative signals by a remote sleep technician. In a further preferred embodiment, the control circuitry and software of polysomnographic monitor 30 are also responsive to control signals from host unit 20 for controlling the operation of auxiliary therapeutic device 46, which is connectable to polysomnographic monitor 30 via auxiliary port 44, thereby allowing remote operation of the therapeutic device 46 by a sleep therapist from host unit 20.

In particular, where auxiliary therapeutic device 46 is a pressure support unit, the inhalation and exhalation pressures and flow rate may be set by the local or remote operator using remote polysomnographic monitor 30 as a control signal interface for bi-directionally communicating with therapeutic device 46. Polysomnographic monitor 30 also receives data from therapeutic device 46, including actual delivery pressures and flow, so that the actual pressure settings of the therapeutic device are provided to the local or remote operator. In the prior art, the pressure settings from the pressure support device have been estimated based upon analog waveforms from the flow sensors of the pressure support device. By controlling the pressure support device from the primary unit, the specific pressure values can be obtained increasing the accuracy with which the pressure support device may be controlled.

Figure 3:
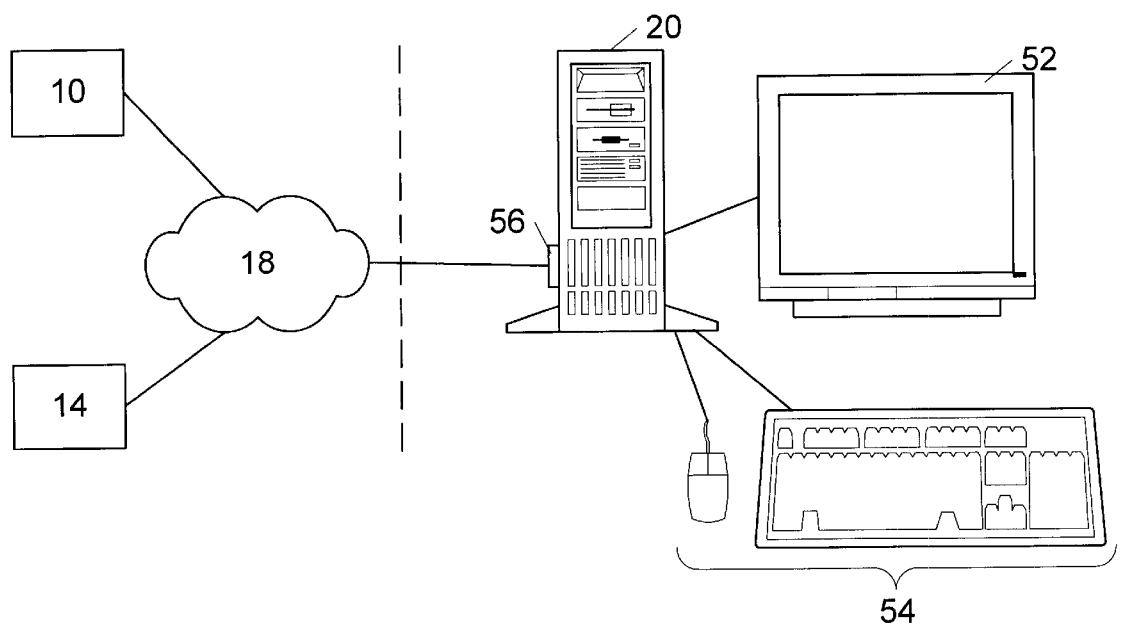
FIG. 3 is a schematic view of a host unit in accordance with the a preferred embodiment of the present invention.

As shown in FIG. 3, host unit 20 includes a central processor 50 having at least one display 52, an input device 54, and a host communication interface 56 for allowing bi-directional communication of signals to and from remote polysomnographic units 10 and 14 via communication network 18. Host unit 20 should also preferably include a data storage unit for storing patient physiological data and for providing a record of issued therapeutic and sensor control instructions. In one preferred embodiment, host unit 20 includes an IBM PC® compatible microcomputer having a Intel Pentium® based microprocessor with at least 32 megabytes of random access memory (RAM) and a 4 gigabyte or greater hard drive, operating a Microsoft Windows 95® based operating system. In the preferred embodiment, display 52 comprises a standard computer monitor, input device 54 comprises a standard keyboard and mouse, and host communication interface 56 comprises an Ethernet-type network interface card. However, one of ordinary skill in the art will recognize that many other processors and operating systems are adaptable to perform the functions of host unit 20.

Host unit 20 includes analysis, display and control software for processing patient physiological data into a format suitable for display to a sleep technician via display 52 and for allowing the sleep technician to relay control commands to remote polysomnographic units 10 and 14. Host unit 20 is adapted to bi-directionally communicate data and control signals with at least two remote polysomnographic units 10 and 14, but is also capable of controlling a single remote polysomnographic unit if so desired.

Figure 4:
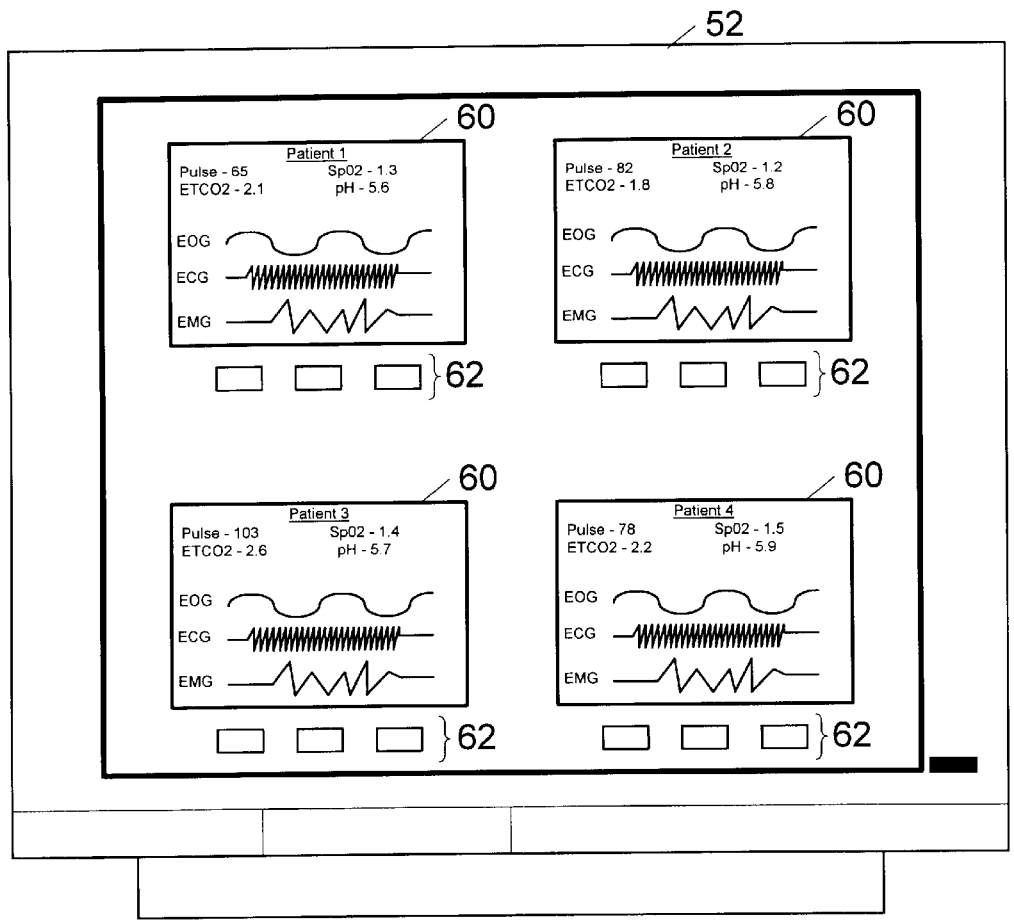
FIG. 4 is a front view of a host unit display operating in "echo mode" according to a preferred embodiment of the present invention.
Figure 5:
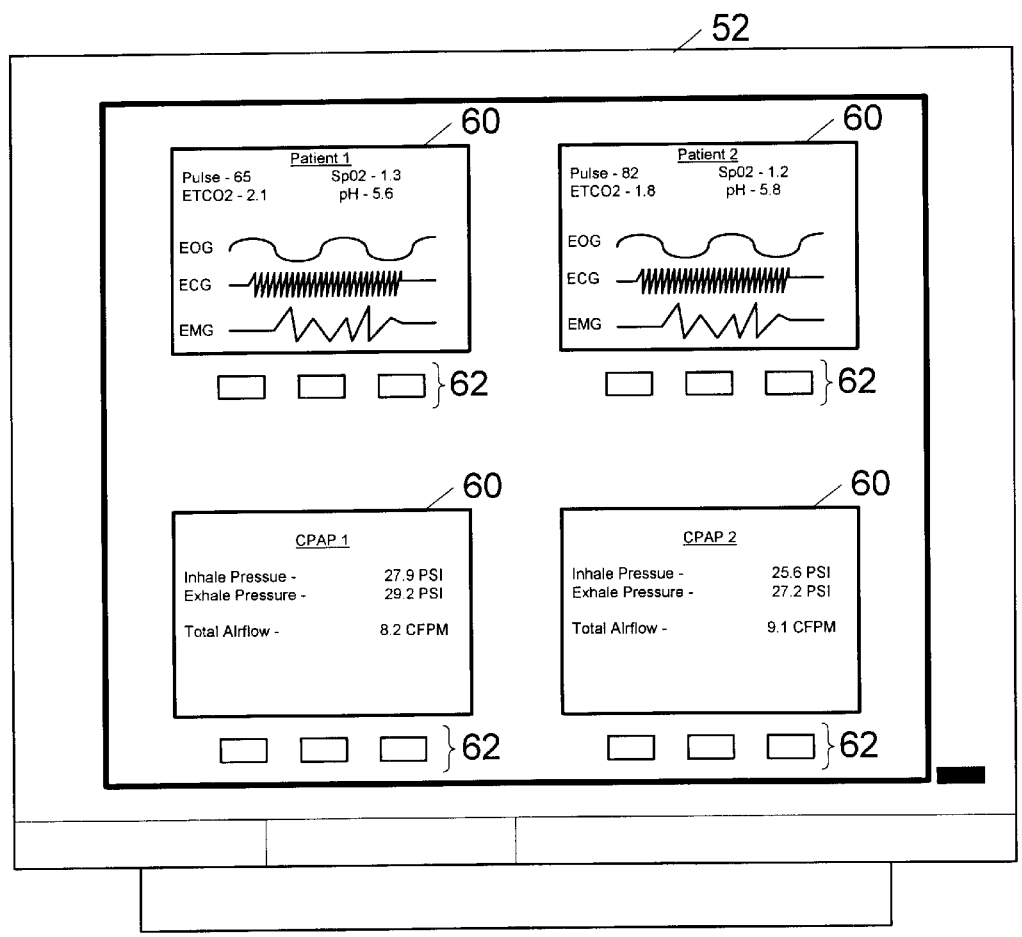
FIG. 5 is a front view of a host unit display operating two polysomnographic devices and respective pressure support devices according to a preferred embodiment of the present invention.

As shown in FIGS. 4 and 5, in a preferred embodiment, host unit 20 may be configured to display, on host display 52, a duplicate version or "echo" 60 of the data simultaneously displayed on the local display 36 of a remote polysomnographic unit 12. This mode is identified as the "echo mode". When networked to a plurality of remote polysomnographic units 12, host unit 20 can display up to thirty-two echo mode screens 60 displaying either patient physiological data or therapeutic device operational data. However, due to the size and resolution limitations of host display 52, it is desirable to limit the number of displayed screens to less than the maximum number. When operating in echo mode, a single sleep technician may utilize host unit 20 to view the ongoing sleep studies of several patients simultaneously. Additionally, a single technician may manipulate, via input device 54 or an optional touchscreen input, the gas flow and delivery pressures of respective pressure support devices for the individual patients for evaluating the correct prescription of pressure support treatment for each individual patient. This system enables a single operator at a remote location to simultaneously undertake several sleep studies. It should be noted that host unit 20 may be networked to multiple remote polysomnographic units 10 and 14 at remote locations via communication network 18.

Thus, in operation, it is contemplated that a single sleep technician at a central location can monitor a plurality of patients undergoing a sleep study at a sleep research facility. It is further contemplated that remote polysomnographic units 10 may also be installed at the homes of patients prior to initiation of an overnight sleep study. The patients will, thus, be able to sleep in familiar surroundings during the sleep study, thereby minimizing the disruption to their sleep patterns which might occur in the more artificial surroundings of a medical or research facility. The sleep technician at a central location may then monitor and, if necessary, remotely adjust the operation of therapeutic devices such as a pressure support device at the remote locations. The technician may then, via the host unit, remotely monitor the effects of the adjustments and readjust as necessary to optimize the therapy provided to each individual patient.

Thus, it may be seen, that an advantageous system and method for allowing a single sleep technician to monitor a plurality of patients is provided according to the present invention. The use of a host unit operatively connected with a plurality of remote polysomnographic units via a communication network allows a single sleep technician to easily and effectively monitor several patients undergoing simultaneous sleep studies. By using the host unit of the present method, the sleep technician is also able to alter the operating parameters of therapeutic devices such as a pressure support device to allow simultaneous calibration and optimization of treatment for a plurality of patients.

It thus will be appreciated that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. A polysomnographic system for use in conjunction with a communications network, said polysomnographic system comprising:

a first remote unit for collecting physiological data from a first patient, said first remote unit including a first sensor for detecting a physiological parameter of such a first patient and generating a first parameter indicating signal in response thereto, and a first communications interface for communicating said first parameter indicating signal to a communications network;

a second remote unit for collecting physiological data from a second patient, said second remote unit including a second sensor for detecting a physiological parameter of such a second patient and generating a second parameter indicating signal in response thereto, and a second communications interface for communicating said second parameter indicating signal to a communications network;

a host unit for receiving said first and second parameter indicating signals via a communication network and for displaying information indicative of said first and second parameters to an operator; and said host unit operable in conjunction with a first pressure support unit to control the delivery of breathing gas to such a first patient.

2. The polysomnographic system of claim 1, wherein said host unit is further operable in conjunction with a second pressure support unit to control the delivery of breathing gas to such a second patient.

3. The polysomnographic system of claim 1, wherein said host unit further comprises a data storage unit for storing data representative of the values of said first and second parameter indicative signals.

4. The polysomnographic system of claim 1, wherein said first and second parameters are displayed simultaneously by said host unit to an operator.

5. A host unit for allowing an operator to monitor a plurality of remote polysomnographic devices, wherein each remote polysomnographic device generates a signal indicative of a physiological parameter of a patient for transmission over a communications network, said host unit comprising:

a communication interface for receiving a plurality of parameter indicative signals from a plurality of polysomnographic units via a communication network;

a processor for selecting a desired parameter indicative signal from said plurality of parameter indicative signals and manipulating said desired parameter indicative signal into a displayable format;

a display for communicating said formatted signal to an operator; and said host unit operating in conjunction with a first pressure support unit to control the delivery of breathing gas to a first patient.

6. The host unit of claim 5, wherein said host unit is further operable in conjunction with a second pressure support unit to control the delivery of breathing gas to a second first patient.

7. The host unit of claim 5, wherein said processor is adapted to simultaneously select a plurality of desired parameter indicative signals and manipulate said plurality of desired parameter indicative signal into a displayable format; and said display is adapted to simultaneously displaying said plurality of formatted signals to an operator.

8. A method for determining an effective positive pressure treatment regimen for treating the occurrence of obstructive sleep apnea, said method comprising the steps of:

providing a first polysomnographic device;

providing a second polysomnographic device;

providing a first pressure support device for delivering breathing gas to a first patient;

providing a second pressure support device for delivering breathing gas to a second patient;

providing a host unit;

sensing a first physiological parameter of such a first patient via said first polysomnographic device;

sensing a second physiological parameter of such a second patient via said second polysomnographic device;

receiving data indicative of said physiological parameters of such first and second patients from said first and second respective polysomnographic devices via said host unit; and displaying said data indicative of physiological parameters of such first and second patients to an operator via said host unit; and adjusting the operating parameters of said first pressure support device via said host unit to determine a pressure support therapy to be administered to such a first patient.

9. The method of claim 8, further including the step of adjusting the operating parameters of said second pressure support device to determine a pressure support therapy to be administered to such a second patient.

10. A method for simultaneously determining an effective pressure support treatment for each of a plurality of patients, said method comprising the steps of:

utilizing a host unit to simultaneously monitor (a) a physiological parameter of a first patient while such a first patient is receiving a therapeutic supply of breathing gas under an initial delivery condition and (b) a physiological parameter of a second patient while such a second patient is receiving a therapeutic supply of breathing gas under an initial delivery condition;

adjusting, via said host unit, the therapeutic delivery of breathing gas to such a first patient in response to said monitored physiological parameter of such a first patient to determine an effective pressure support treatment for such a first patient;

adjusting, via said host unit, the therapeutic delivery of breathing gas to such a second patient in response to said monitored physiological parameter of such a second patient to determine an effective pressure support treatment for such a second patient; and continuing to monitor, via said host unit, said physiological parameters of such first and second patients to monitor the effectiveness of said adjusting steps.

* * * * *